Feb. 19, 1974 G. J. BUCK Plant Pat. 3,489
ROSE PLANT
Filed Oct. 4 1972
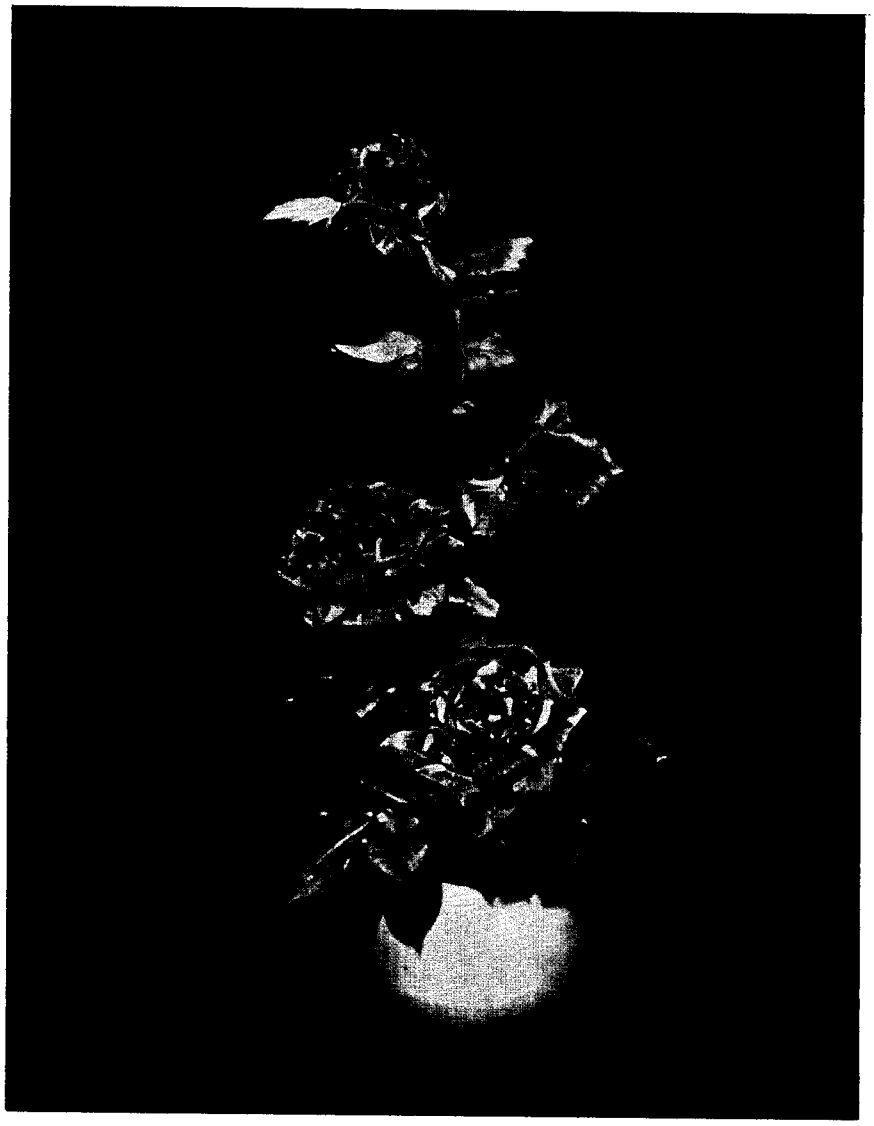

United States Patent Office

Plant Pat. 3,489
Patented Feb. 19, 1974

3,489
ROSE PLANT

Griffith J. Buck, Ames, Iowa, assignor to Iowa State University Research Foundation, Inc., Ames, Iowa Filed Oct. 4, 1972, Ser. No. 290,511
Int. Cl. A01h 5/00
U.S. Cl. Plt.—13 1 Claim

ABSTRACT OF THE DISCLOSURE

A new variety of rose plant characterized by its profuse production of medium sized blooms having a generally cardinal red color with the petal surface irregularly variegated with stripes or patches of varying hues of white, rose and light red coloring. This new rose is further distinguished by its ability to transmit the characteristic color striping or streaking of its flower petals to its own seedlings and by its resistance to low winter temperatures and the high nighttime temperatures of summer.

BACKGROUND OF THE NEW PLANT

This new variety of rose plant originated in 1968 as a seedling of Parks Scarlet Royal x Rouge Mallerin (both unpatented) bred by me at Ames, Iowa, in the course of breeding efforts carried on by me since 1949 with the object of developing improved rose varieties having greater plant resistance to low wintertime temperatures and the high night temperatures of summer. This new plant was observed to possess the desired temperature resistance characteristics, as well as an unusual and attractive flower, and subsequent asexual propagation by means of cuttings and bud grafting carried on by me at Ames, Iowa, has shown these characteristics to hold true from generation to generation and to be firmly fixed.

DESCRIPTION OF THE DRAWINGS

My new variety of rose plant is illustrated by the accompanying full color drawings which show the form and color characteristics of the foliage and blooms of the new plant as nearly true as it is reasonably possible to obtain by conventional photographic procedures.

DESCRIPTION OF THE NEW PLANT

The following is a detailed description of the new variety of rose plant with the color designations according to the R.H.S. Colour Chart of the Royal Horticultural Society at London, England.

*The plant*

Origin: Seedling
Parentage:
- *Seed parent.*—Park's Scarlet Royal (unpatented)
- *Pollen parent.*—Rouge Mallerin (unpatented)

Classification:
- *Botanic.*—Rosa
- *Commercial.*—Hybrid tea

Form: Bush
Height: 75 to 95 cm.
Growth: Moderately vigorous and erect, moderately branching with strong, upright canes
Foliage: Quantity—moderate with 50 to 75 leaves per plant
- *Leaf size.*—Medium—13 to 15 cm. long
- *Leaf Form.*—Odd pinnate

- *Leaflets.*—Number, 5 to 7
- *Shape.*—Ovate with serrate margins and mucronate tip
- *Texture.*—Leathery and smooth
- *Color.*—Upper side—Green 136A. Under side—Green 137C with faint reddish tinge
- *Petioles.*—2–3 cm. long
- *Ribs and veins.*—Pinnate
- *Rachis.*—Prickly
- *Prickles.*—Size—1 cm. long. Color—Greyed-Purple 183A

*The bud*

Form: Round—ovoid
Size: Medium—small
- *Diameters.*—2.5 to 3 cm.
- *Depth.*—3–4 cm.

Opening rate. Bud opens slowly
Color:
- *When sepals first divide*—Greyed-Purple 187A
- *When petals begin to unfurl.*—Greyed-Purple 187C Sepals: Spear shaped, recurved and persistent.
- *Color.*—Inside—Yellow-Green 146B tinted with Greyed-Orange 176B. Outside—Yellow-Green 146B Calyx:
- *Shape.*—Rounded-funnel shape
- *Size.*—Small
- *Aspect.*—Smooth
- *Splitting.*—None Peduncle: Erect, 5–6 cm. long and smooth
- *Color.*—Yellow-Green 148A tinged with Greyed-Red 178A

*The flower*

Blooming: Profuse and continuous from early June until frost
Size of bloom: Medium. 10 to 12 cm. in diameter and 4 to 5 cm. in depth
Borne: Usually singly. Occasionally in cluster
Shape: Cup shaped when bloom first opens, becoming flat as flower matures
Petalage: 50 to 60 petals, including petaloids
- *Arrangement.*—Informal
- *Form.*—Broadly cordate
- *Color.*—Outer petal—Greyed-Purple 187C with streaks and patches of Greyed-Purple 185B, C and D, 186A and 187D. Inside Petal—Greyed-Purple 187C. Reverside side—Greyed-Purple 187D
- *Appearance.*—Velvety
- *Persistence.*—Petals hang on until removed Peduncle: 5 to 6 cm. long. Sturdy, upright and of green color
Discoloration: Blackens in wet weather
Disease resistance: Moderately resistant to Blackspot, as observed in growing areas where the disease is present
Fragrance: Intensely fragrant—"Damask" type
Lasting quality:
- *On plant.*—5 days
- *As cut flower.*—7 days

*Reproductive organs*

Stamens:
- *Anthers.*—Arrangement—ring around pistils. Length—2 mm. Number—75 to 100
- *Filaments.*—Length—5 to 6 mm. Color—Reddish Yellow

*Pollen.*—Color—Yellow Orange
Pistils: Many in number, 5 to 6 cm. long
Stigmas: Color—Reddish Brown
Ovaries: Typically Rosa type, attached to receptacle wall
Fruit: Sparingly fertile, ovoid in shape and of Yellow Orange color when mature.

This new variety of hybrid tea rose most nearly resembles its pollen plant parent Rouge Mallerin, except for the variegation of the flower petals, and a particular distinction of the new variety is that it is the first with variegated flower petals to be derived from seed. Also, this plant has been found to be capable of transmitting its distinctive petal variegation to its own seedlings.

I claim:

1. A new and distinctive variety of rose plant, substantially as herein shown and described, characterized by the variegated color of its well formed blossoms, its profuse and continuous flowering habit, and its resistance to low winter temperatures and high summertime night temperatures.

No references cited.

ROBERT E. BAGWILL, Primary Examiner